(12) United States Patent
McPeak et al.

(10) Patent No.: US 6,303,586 B1
(45) Date of Patent: Oct. 16, 2001

(54) SUPPORTIVE THERAPY FOR DIABETES, HYPERGLYCEMIA AND HYPOGLYCEMIA

(75) Inventors: Patricia McPeak, El Dorado Hills; Rukmini Cheruvanky, Folsom; Reddy Sastry V. Cherukuri, El Dorado Hills, all of CA (US)

(73) Assignee: The RiceX Company, El Dorado Hills, CA (US)

(*) Notice: Subject to any disclaimer, the term of this patent is extended or adjusted under 35 U.S.C. 154(b) by 24 days.

(21) Appl. No.: 09/143,429

(22) Filed: Aug. 28, 1998

Related U.S. Application Data
(60) Provisional application No. 60/057,409, filed on Aug. 29, 1997.

(51) Int. Cl.$^7$ .......................... A61K 31/715; A23L 1/36; A23L 1/168; A23L 1/172; A23L 1/18
(52) U.S. Cl. .............................. 514/54; 514/866; 426/93; 426/618; 426/629
(58) Field of Search .................. 514/54, 866; 426/93, 426/618, 629

(56) References Cited

U.S. PATENT DOCUMENTS

| | | | |
|---|---|---|---|
| 4,358,462 | 11/1982 | Takeda | 426/13 |
| 4,952,568 | 8/1990 | Sawai et al. | 514/103 |
| 5,118,503 | 6/1992 | Sawai et al. | 424/195.1 |
| 5,153,019 | 10/1992 | Hammond | 426/590 |
| 5,292,537 | 3/1994 | Hammond | 426/44 |
| 5,376,390 | 12/1994 | Hammond | 426/44 |
| 5,512,307 | 4/1996 | Hammond | 426/44 |
| 5,514,398 | 5/1996 | Imae et al. | 426/271 |
| 5,591,772 | 1/1997 | Lane et al. | 514/458 |
| 5,753,283 | 5/1998 | Hammond | 426/44 |
| 5,821,264 | 10/1998 | Lane et al. | 514/458 |

FOREIGN PATENT DOCUMENTS

| | | | |
|---|---|---|---|
| 0 457 539 B1 | 1/1994 | (EP) | A23L/1/308 |
| 62201821 | * 9/1987 | (JP) . | |
| 62-201821 A | 9/1987 | (JP) | A61K/31/715 |
| 01-066203 A | 3/1989 | (JP) | C08B/37/00 |
| 1066203 | * 3/1989 | (JP) . | |
| WO 93/09777 | 5/1993 | (WO) | A61K/31/355 |
| WO 98/17286 | 4/1998 | (WO) | A61K/31/715 |

OTHER PUBLICATIONS

Hikino et al., Isolation and Hypoglycemic Activity of oryzabrans A, B, C and D, Glycans of Oryza Sativa Bran. Planta Med. Feb. 1988, 54(1), pp. 1–3.*

Mihara, S., "Nakataki water process for separating rice bran components," *Chemical Economy & Engineering Review* 2(9):36–39 and 42 (9/70).

Zombade, et al., "Nutritive value of raw, parboiled, stabilised and deoiled rice bran for growing chicks," *J. Sci. Food Agric.* 34(8):783–788 (8/83).

Yanagawa, et al., "A Method for Estimating Incidence Rates of Onchocerciasis from Skin–Snip Biopsies with Consideration of False Negatives," *Biometrics* 40:301–311 (Jun. 1984).

The Expert Panel, "Report of the National Cholesterol Education Program Expert Panel on Detection, Evaluation, and Treatment of High Blood Cholesterol in Adults," *Arch Intern Med* 148:36–69 (1988).

Cara, L., et al. "Effects of oat bran, rice bran, wheat fiber, and wheat germ on postprandial lipemia in healthy adults," *Am. J. Clin. Nutr.* 55:81–88 (1992).

Marshall, W.E., et al. (editors), *Rice and Science Technology*, "IV. Stabilization and Processing," pp. 390–404 (1994).

Purushothama, S., et al., "Effect of Long Term Feeding of Rice Bran Oil upon Lipids and Lipoproteins in Rats," *Molecular and Cellular Biochemistry* 146(1):63–69 (1995).

Fan, Q., et al., "Nutritional Evaluation of Rice Bran Oil and a Blend with Corn Oil," *Die Nahrung* 39(5–6):490–496 (1995).

Keith Hargrove, Jr., "AIB Research Department Technical Bulletin," *American Institute of Baking Newsletter* 12(2), 1 pg. (Feb. 1990).

Saunders, R. M., "The properties of rice bran as a foodstuff," *Cereal Foods World* 35(7):632–(Jul. 1990).

Slavin, J. L., et al., "Health benefits of rice bran in human nutrition," *Cereal Foods World*, p. 70 (1992).

Hegsted, et al., "Reducing human heart disease risk with rice bran," *Louisiana Agriculture* 36(3):22–24 (Summer 1993).

Glover, M., "FoodEx: Rice product interests major players," *Sacramento Bee*, Feb. 27, 1997.

* cited by examiner

*Primary Examiner*—Gary Geist
*Assistant Examiner*—Everett White
(74) *Attorney, Agent, or Firm*—Townsend and Townsend and Crew LLP

(57) ABSTRACT

Methods for controlling serum glucose level in a mammal comprising ingesting a stabilized rice bran derivative selected from the group consisting of a solubilized fraction, an insolubilized fraction, an enzyme treated stabilized rice bran and mixtures thereof, thereby reducing serum glucose level in said mammal.

11 Claims, No Drawings

SUPPORTIVE THERAPY FOR DIABETES, HYPERGLYCEMIA AND HYPOGLYCEMIA

RELATED APPLICATIONS

The present application is related to U.S. patent application Ser. No. 60/057,409, filed Aug. 29, 1997, the teachings of which are incorporated herein by reference.

FIELD OF INVENTION

The present invention relates to methods for controlling serum glucose levels in mammals.

BACKGROUND OF THE INVENTION

Diabetes is a chronic disease that has no cure. It affects 16 million people in the U.S. and more than 125 million people worldwide. Diabetes is the fourth-leading cause of death by disease in the United States. In 1997, more than 178,000 people died from the disease and its relates complications.

Diabetes mellitus is characterized by an impaired ability to metabolize carbohydrates, increased glucose in the blood, and excretion of glucose in the urine. This defect involves interference with insulin in its role of facilitating uptake of glucose by cells, to give energy as ATP.

In people with diabetes, the pancreas produces insufficient or no insulin, the hormone which is responsible for the absorption of glucose into cells for energy needs. As a result, the level of glucose in the blood becomes abnormally high, causing excessive urination and constant thirst and hunger. The body's inability to store or use glucose causes weight loss and fatigue. Diabetes mellitus also results in disordered lipid metabolism and accelerated degeneration of small blood vessels.

There are two main types of diabetes mellitus. Type I which is the more severe form, usually first appears in people under the age of 35 and most commonly in people between the ages of 10 and 16. It develops rapidly. The insulin-secreting cells in the pancreas are destroyed, probably as a result of an immune response after a virus infection, and insulin production ceases almost completely. Without regular injections of insulin the sufferer lapses into a coma and dies. Type I diabetes results from the pathological error due to the inability of beta cells of the islets of Langerhans to secrete insulin. It may be due to a genetic disposition or a viral infection, wherein the beta cells are suppressed and are unable to secrete insulin. Individuals suffering from Type I diabetes are totally insulin dependent and is normally manifested by age 25.

The most prevalent type of diabetes, Type II diabetes, is usually of gradual onset and occurs mainly in people over 40. In many cases it is discovered only during a routine medical examination. Patients with Type II diabetes have this condition due to pathological error of malabsorption of glucose or impaired utilization of peripheral insulin or due to the result of abnormal erythrocyte receptors (partly genetic), accounts to absorption/utilization of glucose/insulin. Not enough insulin is produced to meet the body's needs, especially when the person is overweight. Often the body is resistant to the effects of insulin as the receptors are deactivated. In most cases, insulin-replacement injections are not initially required. The combination of dietary measures, weight reduction and oral medication can keep the condition under control for a period of time, but most people with Type II diabetes ultimately require insulin injections.

One of the complications of Type I and Type II diabetes is production of abnormal glycated compounds. Glycation and glycoxidation, a sequential process, is often encountered in uncontrolled Type I and Type II diabetics. This involves the surface protein of LDL, and its component apolipoprotein B, which contributes to atherogenicity. Glycated and glycoxidated products are chemotactic to monocytes. The monocytes in the vascular cells infiltrate to macrophage, and form foam cells in the vascular collagen, facilitating adhesion of lipoproteins, suppressing immune complexes and resulting in atherosclerotic plaques. Lysine-fructose in blood is an indicator of the extent of glycation before and after treatment. Carbomethoxy lysine in serum is an indicator of the extent of glycoxidation—before and after treatment.

In patients with Type II diabetes, there is an imbalance between oxidants and antioxidants leading to endothelial dysfunction, which can predispose the patients to atherosclerosis and target organ damage. The levels of lipid peroxidation are high with simultaneous decrease in those antioxidants such as superoxide dismutase, Vitamin E, glutathione peroxidase, methionine reductase and nitric oxide.

The long-term complications of the disease usually are a decreased life expectancy, neuropathy, and an increased rate of blindness (by 25 times), an increased rate of kidney disease (by 17 times) and an increased rate of heart disease (2 times) in comparison to nondiabetics. Type I and Type II diabetics are always associated with hypercholesterolemia and hyperlipidemia.

As stated above, diabetes may be controlled with insulin and in some cases through careful diet. However, the blood sugar levels will still fluctuate (sometimes dramatically), in patients undergoing insulin or diet therapy. Furthermore, in cases where the diabetes is severe, patients find it necessary to constantly monitor their glucose levels to prevent associated illnesses. Diabetic patients are forced to inject insulin which ultimately leads to bruising in certain areas. Furthermore, additional medical complications often arise from diabetes such as arteriosclerosis, hyperlipidemia, retinal damage, neurological damage, fatigue and weakness.

Therefore, there is a need for a safe and effective treatment for diabetes with minimal side effects and without the invasive procedures, such as injections. In addition, there remains a need for a treatment which addresses other medical ailments which often accompany diabetes, to insure that patients remain in the best health possible. The present invention fulfills these and other needs.

SUMMARY OF THE INVENTION

In some instance, conventional therapy for diabetes is to administer one or more injections per day of various forms of insulin while monitoring blood glucose levels. Near normal blood sugar levels are difficult if not impossible to achieve using conventional therapy. There exists a great need for additional therapy for diabetes to control serum glucose level. It has now been surprisingly found that ingesting stabilized rice bran derivatives control serum glucose levels in mammals. As such, in one aspect, the present invention relates to methods for reducing serum glucose level in mammals by ingesting a stabilized rice bran derivative, such as an enzyme treated stabilized rice bran, a solubilized fraction, an insolubilized fraction or mixtures thereof. In one embodiment, the rice bran derivative is ingested in an amount of about 10 grams to about 100 grams per day total, preferably in at least 2 doses.

In another aspect, the present invention relates to methods for managing hyperglycemia in mammals, by ingesting a stabilized rice bran derivative such as an enzyme treated stabilized rice bran, a solubilized fraction, an insolubilized fraction and mixtures thereof.

In still other aspects, the present invention relates to a diabetic food supplement kit comprising a stabilized rice bran derivative, such as an enzyme treated stabilized rice bran, a solubilized fraction, an insolubilized fraction and mixtures thereof, a non-rice consumable, and instructions for the use of the components of the kit. Additional embodiments will be apparent to those skilled in the art with reference to the following detailed description.

DESCRIPTION OF THE PREFERRED EMBODIMENT

I. Glossary

As used herein the term "apolipoprotein B" or "apoprotein B" or "Apo B" refers to the protein component of the cholesterol transport proteins. Cholesterol synthesized de novo is transported from the liver and intestine to peripheral tissues in the form of lipoproteins. Most of the apolipoprotein B is secreted into the circulatory system as VLDL.

As used herein the term "arteriosclerosis" is a degeneration of the walls of the arteries due to the formation of foam cells and aortic streaks which narrow the arteries. This limits blood circulation and predisposes an individual to thrombosis.

As used herein the term "enzyme treated stabilized rice bran derivative" refers to an enzyme treated stabilized rice bran made by mixing a stabilized rice bran with an aqueous solution in a 15% to about a 35% aqueous slurry w/w; adding an enzyme to the aqueous rice bran slurry to convert starch to dextrin, and then directly drying the dextrin solution to form an enzyme treated stabilized rice bran derivative. The enzyme treated stabilized rice bran comprises about 20% to about 30% total dietary fiber.

As used herein the term "GRAS" means generally regarded as safe with respect to food additives.

As used herein the term "hypercholesterolemia" is a condition with elevated levels of circulating total cholesterol, LDL-cholesterol and VLDL-cholesterol as per the guidelines of the Expert Panel Report of the National Cholesterol Educational Program (NCEP) of Detection, Evaluation of Treatment of high cholesterol in adults (see, Arch. Int. Med. (1988) 148, 36–39).

As used herein the term "hyperglycemia" refers to an excess of glucose in the bloodstream. It can occur in a variety of diseases due to insufficient insulin in the bloodstream and excessive intake of simple carbohydrates.

As used herein the term "hypoglycemia" refers to a deficiency of glucose in the bloodstream. If sever, this can lead to a hypoglycemic coma.

As used herein the term "hyperlipidemia" or "hyperlipemia" is a condition where the blood lipid parameters are elevated in the blood. This condition manifests an abnormally high concentration of fats. The lipids fractions in the circulating blood are, total cholesterol, low density lipoproteins, very low density lipoproteins and triglycerides.

As used herein the term "lipoprotein" such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

As used herein the term "stabilized rice bran derivative insolubilized fraction" refers to a fraction during a partitioning process. Specifically, after the stabilized rice bran aqueous slurry is enzymatically treated, it is then pumped into a horizontal centrifuge where the insoluble fraction precipitates out of the aqueous solution. The insoluble fraction is collected and then dried, and subsequently ground into a powder. This powder is the insoluble portion. The constituent parts and their percentages are listed in Tables I and IV.

As used herein the term "stabilized rice bran derivative solubilized fraction" refers to a fraction during a partitioning process. Specifically, after the stabilized rice bran aqueous slurry is enzymatically treated, it is then pumped into a centrifuge where the insoluble fraction precipitates out of the aqueous solution. The aqueous material is pumped to a dryer and then dried. This dried aqueous portion produces the soluble fraction. The constituent parts and their percentages are listed in Tables I and V.

As used herein the term "triglyceride" means a lipid or neutral fat consisting of glycerol combined with three fatty acid molecules.

II. Detailed Description

In harvested rice, also known as rough rice, the kernel is completely enveloped by the rice hull. The milling process removes the hull, which yields brown rice. The outer brown layer is then removed by an abrasive milling process to generate white rice. The separated brown layer is designated rice bran.

Rice bran is the mesocarp, i.e., the portion between the hull and rice grain, obtained by milling or polishing brown rice. It constitutes about 10% of rough rice. It is generally used as an animal feed. It contains about 18–24% fat, about 25% dietary fiber, about 14% protein and about 45% total carbohydrates besides several potent micronutrients. It is rich in B-complex vitamins, vitamin E and its isomers, minerals like potassium, magnesium, and phosphorous besides several potent antioxidants.

Stabilized rice bran can be commercially purchased or prepared using various methods. Most stabilization methods of rice bran result in inactivation of the lipases which are present, inactivation of the peroxidases, and inactivation of the microorganisms, while still maintaining the high levels of antioxidants in the rice bran. For a general discussion of stabilization and processing see, *Rice Science and Technology*, edited by W. E. Marshall and James I Wadswoth, (1994) pages 390–404.

Under normal conditions when brown rice is milled to rice, the oil in the bran and the lipases also in the bran come into mutual contact, resulting in rapid degradation of the rice oil to free fatty acids and glycerol. The rice bran becomes unpalatable and is no longer suitable for foodstuffs. However, if the lipases are inactivated, the rice bran is thereby stabilized and the adverse effects on the bran are avoided.

There are many suitable means to stabilize or inactivate the lipase in rice bran, however most commercial systems utilize moisture-added or dry extrusion methods. These systems are selected because of their relatively low energy requirements, low capital costs and ease of operation. Stabilization by dry extrusion utilizes shear, friction, and pressure to generate the heat required to inactivate the lipase.

The temperature of the bran must reach a temperature of a minimum of 130°–140° C. for up to 3 seconds to assure inactivation of the lipase. Acceptable extrusion stabilization can be achieved under less harsh conditions by adding water or steam. The lipase is more heat sensitive at higher moisture and can therefore be inactivated at somewhat lower extrusion temperatures.

Residual peroxidase activity is generally used as the standard measure to make sure that lipase activity has been deactivated in stabilized rice bran. Peroxidase is generally considered to be more heat stable than lipase, and peroxidase activity assays are easier and more reliable than the assays for lipase. The process conditions required to inactivate peroxidase as well as lipase can also cause modification to or loss of antioxidants in the bran. This can lead to fewer fatty acids, but the bran can be subject to oxidative rancidity. In addition, because the rice bran is susceptible to mold, yeast and bacteria, the stabilization process must effectively reduce the microbiological load of the bran.

In addition to moisture added and extrusion techniques for stabilization, freezing and refrigeration of the rice bran result in economically viable processes to stabilize rice bran. Preferably, processes used to stabilize rice bran minimize the free fatty acid content, while maintaining high levels of antioxidants. Food grade stabilized rice bran is typically finely granulated, light tan in color and possesses a relatively bland flavor with a nutty, toasted overtones.

Stabilized rice bran is available commercially from Producers Rice Mill Inc. (Stuttgart, Ark.), Riceland Foods (Stuttgart, Ark.), Riviana Foods, Inc. (Houston, Tex.), Uncle Ben's Inc. (Houston, Tex.) and The RiceX Company (El Dorado Hills, Calif.). Due to different stabilization processes, stabilized rice bran will differ in composition and stabilization characteristics when derived from different manufacturers.

In order to generate the rice bran derivatives for use in the present invention, the rice bran is first stabilized, and then it is further separated into at least two fractions. These include, but are not limited to, a stabilized rice bran soluble derivative and a stabilized rice bran insoluble derivative. Preferably, the separation into the rice bran derivatives includes a nonchemical process i.e., an enzymatic process. In this process, partitioning or fractionation preferably proceeds as outlined hereinafter.

The stabilized rice bran is made into about a 15% to about a 35% slurry, preferably, 20–25% slurry with potable water. An enzyme, which can include, but is not limited to, a dextranase, a maltase, a α-amylase, and various other carbohydrate cleaving enzymes, is added to the batch converting the starch to dextrins. The slurry is heated to about 150° F. to about 200° F. using for instance, a steam injection cooker, a heat exchanger, or other heating method. The slurry is then pumped to a horizontal centrifuge wherein the insoluble fraction is separated. The insoluble fraction is collected and then dried on a belt dryer, and subsequently ground into a powder. This powder is the stabilized rice bran insoluble fraction. The aqueous material is pumped to a drum dryer and then dried. This dried aqueous portion produces the stabilized rice bran solubilized fraction.

The enzyme treated stabilized rice bran can be generated using the rice bran slurry as described above. As such, in another aspect, the present invention relates to the process for making an enzyme treated stabilized rice bran derivative, comprising: admixing stabilized rice bran with an aqueous solution to form about a 15% to about a 35% aqueous rice bran slurry, preferably a 20% to about a 30% aqueous rice bran slurry w/w; adding an enzyme to the aqueous rice bran slurry to convert starch to dextrin, thereby forming an enzyme treated slurry, and then directly drying the enzyme treated slurry to form an enzyme treated stabilized rice bran derivative.

In a preferred embodiment of the foregoing process, after the enzyme is added to the slurry, the slurry is heated to about 100° F. to about 200° F. Preferably, the slurry is heated to about 150° F. to about 200° F. The slurry is then dried, wherein the drying is accomplished by a process such as belt drying, spray drying, drum drying and air drying. The drum drying process is preferred.

These stabilized rice bran derivatives are also available commercially from The RiceX Company of California. For the purpose of the invention, stabilized rice bran is available as RiceX™ Stabilized Rice Bran. The insoluble derivative is available as RiceX™ Fiber Complex and the soluble derivative is available as RiceX Ricelin™ from The RiceX Company, El Dorado Hills, Calif.

The stabilized rice bran derivatives can take a variety of forms. They can be a powder, a food, a food supplement, a medical food, a liquid, a beverage, an emulsion or mixture thereof. In addition, they can be incorporated into other edible materials. To incorporate the rice bran derivative into the diet of a mammal various options include, but are not limited to, simply sprinkling the derivative on another food substance (i.e., salad, bread, cereal, etc.) being a major ingredient in a multigrain ready to eat cereal, incorporating it into a baked product (breads, muffins, waffles, etc), pasta, healthy dessert and snacks (athletic bar, healthy drink, etc.) and high fiber foods.

Stabilized rice bran contains about 18–23% fat, about 23–35% dietary fiber, about 12–16% protein, about 8–36% total carbohydrate and many potent mnicrocomponents. Rice bran solubles contains about 15–40% fat, preferably 23–30% fat; about 0% to 25% dietary fiber, preferably about 0–20% dietary fiber; about 0% to 15% protein, preferably 6–9% protein and 25% to about 80% carbohydrates, preferably about 27–66% simple carbohydrate and is a water soluble fraction. Stabilized rice bran insoluble derivative contains about 5%–20% fat, preferably 11–16% fat; about 40–65% dietary fiber, preferably 40–60% dietary fiber, and about 10–30% protein, preferably 18–22% protein (see, Table I)

TABLE I

| COMPOSITION (est.) | |
|---|---|
| RiceX ™ Stabilized Rice Bran | |
| Fat | 18–23% |
| Protein | 12–16% |
| Total Dietary Fiber | 23–35% |
| Soluble Fiber | 2–6% |
| Carbohydrates | 8–36% |
| Ash | 7–10% |
| Moisture | 4–8 |
| RiceX Ricelin ™ | |
| Fat | 23–30% |
| Protein | 6–9% |
| Total Dietary Fiber | 0–20% |
| Carbohydrates | 27–66% |
| Ash | 3–7% |
| Moisture | 2–7% |
| RiceX ™ Fiber Complex | |
| Fat | 11–16% |
| Protein | 18–22% |
| Total Dietary Fiber | 40–60% |
| Soluble Fiber | 0–12% |
| Carbohydrates | 0–12% |
| Ash | 8–12% |
| Moisture | 1–6% |

With reference to Tables IV, V, VI and VII in Example 4, these derivatives have been shown to have at least seventy-five (75) potent anti-oxidants. The major antioxidant vitamin E and its isomers known as tocopherols (T and tocotrienols (T$_3$) are collectively called tocols. A tocol rich substance is a mixture containing one or more compounds selected from tocopherols (T, tocotrienols (T$_3$), and tocotrienol-like (T$_3$-like) compounds.

Antioxidant in stabilized rice bran derivatives include, but are not limited to, γ-oryzanol, β-carotene, several known flavanoids, phytosterols, lipoic acid, and ferulic acid. Some of these compounds are present in high concentration, much more than in any of the known natural sources. It is believed that antioxidants particularly tocols, play a crucial role in significantly correcting certain metabolic disorders singularly or synergistically as discussed below.

The stabilized rice bran soluble derivative is a powdered emulsion of soluble stabilized rice bran and germ, and is easily digested and absorbed by the body. It can be taken by itself with a small amount of water to dissolve it in the mouth. It can also be mixed into liquids such as juice or hot driks. Additionally, it is appropriate for use in baked goods and other foodstuffs as discussed above. There are a significant number of nutrients which have been discovered in rice bran solubles (stabilized rice bran solubilized derivatives).

The stabilized rice bran insoluble derivative binds bile acids thereby lowering serum cholesterol levels and decreases triglyceride levels thereby helping in the metabolism of cholesterol. It contains many highly potent antioxidants such as β-carotene, α, β, γ, and δ tocopherols and tocotrienols, phytate, oryzanols, glycosides and numerous phytosterols and polyphenols. The rice bran insoluble derivative can also be mixed into liquids such as juice or hot drinks. Additionally, it is appropriate for use in baked goods and other foodstuffs as discussed above.

The enzyme treated stabilized rice bran derivative can also be mixed into liquids such as juice or hot drinks. Additionally, it is appropriate for use in baked goods and other foodstuffs as discussed above.

In one aspect, the present invention relates to a method for controlling serum glucose level in mammals comprising ingesting a stabilized rice bran derivative, such as an enzyme treated stabilized rice bran, a solubilized fraction, an insolubilized fraction or mixtures thereof. The preferred mammal is a human individual. In a preferred embodiment, the glucose level is elevated due to diabetes mellitus, such as Type I and Type II diabetes. The rice bran derivative is ingested in an amount of about 10 grams to about 100 grams per day total, preferably in at least 2 doses. Preferably, the rice bran derivative is ingested in an amount of about 10 grams to about 40 grams per day total, and more preferably, in an amount of about 15 grams to about 30 grams per day total.

It is presently preferred to take the stabilized rice bran derivative orally. Although the optimum dosage would be determined by the physician taking into account the age, weight and general health of the subject. As discussed above, the daily dosage can also be ingested in one or several treatments over a period of time, such as by way of single or multiple doses per day or from sustained release compositions.

The present invention is based on the discovery that persons with Type I and Type II diabetes who ingest products containing rice bran derivatives, which is any substance derived from rice bran including, but not limited to, enzyme treated stabilized rice bran, rice bran solubles and rice bran insolubles, have significantly reduced serum glucose levels, thereby controlling blood glucose levels.

In another aspect, the present invention relates to methods for managing hyperglycemia in mammals. The method comprises ingesting a stabilized rice bran derivative such as an enzyme treated stabilized rice bran, a solubilized fraction, an insolubilized fraction and mixtures thereof. The rice bran derivative can be administered alone or, more usually, in the form of a foodstuff comprising a therapeutically effective amount of the active agent in combination with an inert GRAS.

In still another aspect, the present invention relates to a diabetic food supplement kit. The kit comprises a stabilized rice bran derivative, such as an enzyme treated stabilized rice bran, a solubilized fraction, an insolubilized fraction and mixtures thereof, a non-rice consumable, and instructions for ingesting the derivatives. The non-rice consumable can be a carrier for the stabilized rice bran derivative. In addition, the kit also contain instructions for use.

The non-rice consumable can be any of many ways to incorporate the rice bran derivative into the diet of a mammal. These include, but are not limited to, simply sprinkling the derivative on another food substance (salad, bread, cereal, etc.) being a major ingredient in a multigrain ready to eat cereal, incorporating it into a baked product (breads, muffins, waffles, etc), pasta, healthy dessert and snacks (athletic bar, healthy drink, etc.) and high fiber foods. The non-rice consumable can be various food formulations as well, including, but not limited to, carriers and excipients. The rice bran derivatives can also be used in association with other therapeutic agents including, for example, antibiotics or antiviral agents.

Management of Hyperglycemia Diabetes Mellitus and Related Disorders

Stabilized rice bran derivatives are very effective hypoglycemic agents and therefore helpful as nutritional supplements in the management of Diabetes Mellitus (Type I and Type II), hyperglycemia, and related conditions. These biological effects are due to the synergistic effects of the multiple bioactive components present in stabilized rice bran derivatives (see, Table IV–VI). The mechanisms that are effecting glucose maintenance exert their effect differently, with some effecting glucose absorption, utilization and excretion. While not being bound to any particular theory, it is believed that the mechanisms of action of the individual bioactive components in the stabilized rice bran derivatives include, but are not limited to, the following:

1. The role of B vitamins:
   a. Niacin is present in significant quantities in stabilized rice bran derivatives. Niacin is involved in supplying intracellular energy, through nicotinamide adenine dinucleotide (NAD) utilization in the pancreatic β-cells thereby effecting blood glucose levels.
   b. Pyridoxin is a vital component for the prevention of diabetic neuropathy.
   c. Thiamin and biotin are very important metabolic factors in glucose control.
   d. Therefore, B vitamins in stabilized rice bran derivatives improve glucose absorption at the systemic level and/or improve peripheral utilization of glucose thereby aiding in the control of postprandial glycemnia.
2. Inositol has a modulatory role in the regulation of insulin exocytosis thus helping in the insulin secretory process.
3. The non-starchy polysaccharide and ligins present in stabilized rice bran derivatives enhance the immune complexes and activate the insulin receptors on erythrocytes, thereby enhancing the peripheral utilization of glucose.

4. Stabilized rice bran derivatives are rich in hemicelluloses, which increase peripheral blood lymphocytes, thereby reducing the neurological complications of diabetes.
5. The antioxidants such as tocopherols, tocotrienols, γ-oryzanol, polyphenols (especially ferulic acid and lipoic acid), and other minor antioxidants present in stabilized rice bran derivatives are free radical scavengers, that can ameliorate the complications of diabetes such as atherosclerosis, hyperlipidemia, retinopathy, glycation, glycoxidation, kidney damage and neuropathy. γ-Oryzanol improves capillary blood circulation and has a neuro-regulatory effect.
6. The non-starchy polysaccharides present in the soluble fraction of stabilized rice bran derivatives form a micelle in the intestine, which can facilitate slow absorption and release of glucose into circulation thereby helping to maintain postprandial glucose levels.
7. The protein, fiber and fat of stabilized rice bran derivatives also help in the management of hyperglycemia and associated conditions which are significant health management issues in individuals with diabetes.

III. EXAMPLES

Example 1

This example illustrates a clinical evaluation of stabilized rice bran derivatives in subjects with diabetes mellitus. Moreover the effect of RiceX Stabilized Rice Bran, RiceX Ricelin (stabilized rice bran soluble derivative) and RiceX Fiber Complex (stabilized rice bran insoluble derivative) on blood glucose and lipid human subjects with diabetes mellitus (Type I) and non-insulin dependent diabetes mellitus (Type II) was evaluated. This clinical evaluation was carried out at the Advanced Medical Research center at Madison, Wis. and at the Armed Forces Institute of Pathology, Rawalpindi, Pakistan.

MATERIAL AND METHODS:

A. Product Description

RiceX Stabilized Rice Bran, RiceX Ricelin and RiceX Fiber Complex are products rich in fiber, non-starchy polysaccharides, complex carbohydrates, proteins, fats, B-complex vitamins, and potent antioxidants such as β-carotene, vitamin E (Tocopherols and Tocotrienols), γ-oryzanol, phytosterols, and polyphenols.

| B. Product Codes | |
| --- | --- |
| Product A: | RiceX Stabilized Rice Bran; |
| Product B: | RiceX Ricelin; |
| Product C: | RiceX Fiber Complex |

C. Subjects

Subjects selected were individuals with clinically established cases of diabetes mellitus (Type I or Type II), male or female, between the age of 20–65 years, with ideal body weight (+20%), and no diagnosed complications. The subjects were under glycemic control with either oral hypoglycemic agents, or insulin therapy or both. All the subjects were on National Cholesterol Education Program (NCEP) step-1 diet.

D. Dosage and Duration

The subjects were initially screened and randomly assigned to the RiceX product regimen. Test product was provided to each subject in two equally divided doses of 10 grams each, one taken before breakfast and one taken before dinner in milk/fruit juice/water beverage. The total dosage of 20 grams per day was provided to each subject every day for eight weeks.

E. Study Protocol

The products were given at random either in sequence, or individually for eight weeks. When subjects were evaluated on more than one product a washout period of four weeks with a cellulose placebo to replace treatment was used before switching to the next product. An initial fasting blood sample was drawn before each product regimen, and a final fasting blood sample was drawn at the end of each product regimen. These blood samples were used for the measurement of glycemic and lipid parameters. Physical parameters such as body weight, body mass index, height, medications, and diet were measured and recorded for each subject. Blood glucose levels were monitored every morning before breakfast and every evening before dinner, by the subjects drawing capillary blood and using a glucometer. Any significant change, like sudden hypoglycemic episodes were managed by reducing the medications as well as the rice bran products on which the subjects were maintained, as recommended by the study a physician.

F. Biochemical Analysis

The initial and final blood samples of all the subjects before and after the treatment of each product were collected and stored at −80° C. until analyzed. These samples were analyzed for glycosylated hemoglobin, glucose, insulin, total cholesterol, LDL-Cholesterol, HDL-Cholesterol, Apo B, and triglycerides. All methods used were AOAC approved methods.

G. Statistical Analyses of the Data

All the parameters were statistically analyzed, using changes from baseline values (0-time) to the end of study according to analyses of variance (Yanagava et al., *Biometrics*, 40:301–311, 1984.) These data were compared among the three products.

Results

Table II summarizes the study of both Type I subjects on glycemic and lipidemic parameters, while Table III provides the data for the Type II subjects.

H. Type I Study

A total of 45 subjects with clinically established Type I diabetes mellitus were randomly treated with RiceX rice bran products either in sequence or singularly as mentioned above. A total of 22 subjects were treated with product A, 26 subjects with product B and 20 subjects with product C. The pooled averages of the data on glycemic and lipid parameters of the three products are given in Table II.

I. Type II Study

A total of 41 subjects with clinically established Type II diabetes mellitus were randomly treated with RiceX Rice Bran products either singularly or in sequence as given in the protocol. A total of 23 subjects were treated with product A, 31 subjects with product B and 26 subjects with product C. The pooled averages of the data on glycemic and lipid parameters of all the three products are given in Table III.

J. Glycemic control

The results showed that there was a statistically significant (p=0.05) reduction in the glycosylated hemoglobin, by 11% when RiceX Ricelin was provided and by 10% when RiceX Fiber Complex was provided to the Type I subjects for eight weeks. A similar statistically significant (p=0.05) reduction in glycosylated hemoglobin in Type II subjects was shown. RiceX Ricelin consumption for eight weeks led to a 10% reduction in glycosylated hemoglobin, while RiceX Fiber Complex consumption for eight weeks lead to an 11% reduction. Fasting serum glucose indicated a statistically significant (p<0.5) reduction of 33%, when compared to the initial values, after eight weeks consumption of RiceX Ricelin in both Type I and Type II subjects. The RiceX Fiber Complex also showed a decrease in the fasting glucose levels of venous blood analysis of 19% and 22% in Type I and Type II respectively, when compared to initial time values.

Type I subjects who consumed or RiceX Ricelin for eight weeks showed a decrease of 16% and 14% respectively for fasting glucose and glucose measured a ½ hour before dinner (monitored by glucometer). While RiceX Fiber Complex consumption showed a decrease of 10% and 17% respectively for serum fasting glucose and serum glucose measured a ½ hour before dinner (monitored by glucometer).

In Type II subjects a decrease of 8% and 5% in fasting glucose and glucose ½ hr before dinner (monitored by glucometer) with RiceX Ricelin consumption for eight weeks was observed. A 10% reduction in both the parameters with RiceX Fiber Complex was observed.

These data on glycemic parameters indicate that RiceX products significantly control and manage blood glucose levels in diabetes mellitus. More specifically, the reduction of glycosylated hemoglobin indicated that, in these subjects, consumption of RiceX Ricelin and RiceX Fiber Complex aided in increased control of blood glucose.

K. Lipid Parameters

Total cholesterol, LDL-Cholesterol, Apo B, and triglycerides of Type I subjects who consumed RiceX Fiber Complex for eight weeks were reduced 10%, 16%, 10%, and 7% respectively, when compared to zero-time values. There was no change in HDL-Cholesterol.

A greater reduction in lipid parameters was seen in Type II subjects than that noted in Type I subjects. Total cholesterol, LDL-Cholesterol, Apo B, and triglycerides were reduced by 12%, 15%, 10% and 8% respectively when compared to zero-time values. There was no change in HDL-Cholesterol concentrations after the consumption of RiceX Fiber Complex. These results indicate that the RiceX Fiber Complex significantly controls hyperlipidemia.

TABLE II

Results of Type I (IDDM) Subjects

| | Product A (n = 22) | | | Product B (n = 26) | | | Product C (n = 20) | | |
|---|---|---|---|---|---|---|---|---|---|
| | Before | After | % Change | Before | After | % Change | Before | After | % Change |
| Glycemic parameters | | | | | | | | | |
| Phlebotomy Data | | | | | | | | | |
| Glycosylated Hb (%) | 10.91 | 10.92 | 0 | 11.25 | 10.06 | −11 | 11.32 | 10.23 | −10 |
| Fasting Serum Glucose (mg/dl) | 172.00 | 157.99 | −9 | 174.16 | 116.97 | −33 | 162.78 | 131.56 | −19 |
| Serum insulin | 49.36 | 49.71 | 0 | 52.75 | 54.86 | 4 | 52.03 | 51.99 | 0 |
| Glucometer Data | | | | | | | | | |
| Fasting Glucose (mg/dl) | 159.45 | 154.95 | −3 | 162.5 | 137.23 | −16 | 164.95 | 147.85 | −10 |
| Glucose 1/2 hr. before dinner (mg/dl) | 175.00 | 165.91 | −5 | 168.12 | 145.35 | −14 | 175.35 | 144.95 | −17 |
| Lipid Parameters | | | | | | | | | |
| Serum Total Cholesterol (mg/dl) | 181.91 | 180.07 | −1 | 174.27 | 166.14 | −5 | 185.82 | 167.74 | −10 |
| Serum LDL-Cholesterol (mg/dl) | 137.71 | 134.16 | −3 | 130.79 | 122.35 | −6 | 134.41 | 113.55 | −16 |
| Serum Apo B (mg/dl) | 88.15 | 86.15 | −2 | 85.69 | 81.708 | −5/84.37 | 75.96 | −10 | |
| Serum Triglycerides (mg/dl) | 135.36 | 134.85 | 0 | 134.07 | 130.13 | −3 | 129.76 | 120.58 | −7 |
| Serum HDL-Cholesterol (mg/dl) | 37.65 | 37.62 | 0 | 38.73 | 38.07 | −2 | 39.29 | 39.57 | 0 |

TABLE III

Results of Type II (NIDDM) Subjects

| | Product A (n = 23) | | | Product B (n = 31) | | | Product C (n = 26) | | |
|---|---|---|---|---|---|---|---|---|---|
| | Before | After | % Change | Before | After | % Change | Before | After | % Change |
| Glycemic parameters | | | | | | | | | |
| Phlebotomy Data | | | | | | | | | |
| Glycosylated Hb (%) | 10.22 | 10.63 | 4 | 10.69 | 9.65 | −10 | 10.700 | 9.51 | −11 |
| Fasting Serum Glucose (mg/dl) | 158.11 | 142.28 | −10 | 158.18 | 106.52 | −33 | 145.42 | 113.65 | −22 |
| Serum insulin (microunits/ml) | 49.42 | 49.98 | 0 | 48.48 | 50.31 | 4 | 49.45 | 49.94 | 0 |

TABLE III-continued

Results of Type II (NIDDM) Subjects

| | Product A (n = 23) | | | Product B (n = 31) | | | Product C (n = 26) | | |
|---|---|---|---|---|---|---|---|---|---|
| | Before | After | % Change | Before | After | % Change | Before | After | % Change |
| Glucometer Data | | | | | | | | | |
| Fasting Glucose (mg/dl) | 120.13 | 121.71 | 1 | 128.45 | 118.16 | −8 | 129.12 | 115.73 | −10 |
| Glucose 1/2 hr. before dinner (mg/dl) | 120.17 | 129.91 | 8 | 129.68 | 123.61 | −5 | 134.54 | 120.96 | −10 |
| Lipid Parameters | | | | | | | | | |
| Serum Total Cholesterol (mg/dl) | 182.81 | 172.79 | −5 | 181.14 | 171.1 | −6 | 186.04 | 164.58 | −12 |
| Serum LDL-Cholesterol (mg/dl) | 146.02 | 134.97 | −8 | 143.18 | 131.48 | −8 | 146.46 | 124.77 | −15 |
| Serum Apo B (mg/dl) | 95.56 | 94.23 | −1 | 94.92 | 92.27 | −3 | 95.00 | 85.62 | −10 |
| Serum Triglycerides (mg/dl) | 143.75 | 139.13 | −3 | 138.85 | 135.47 | −2 | 143.01 | 131.24 | −8 |
| Serum HDL-Cholesterol (mg/dl) | 36.23 | 36.21 | 0 | 34.42 | 34.33 | 0 | 33.64 | 33.54 | 0 |

Example 2

This example illustrates the synthesis of enzyme treated stabilized rice bran.

Twelve hundred pounds of stabilized rice bran was mixed with five hundred seventy gallons of water to form a water extract. The mixture was allowed to agitate for thirty minutes. Two hundred and forty grams of α-amylase were added and allowed to mix for ten minutes. Thereafter the mixture was pumped through a heat exchanger set at about 190° F. and allowed to travel through a pipe coil for 25 minutes. The mixture was then dried on a drum dryer to a moisture level below 5%.

Example 3

This example illustrates the synthesis of stabilized rice bran insoluble and soluble derivatives.

Twelve hundred pounds of stabilized rice bran was mixed with five hundred seventy gallons of water to form a water extract. The mixture was allowed to agitate for thirty minutes. Two hundred and forty grams of a-amylase were added to the mixture and allowed to mix for ten minutes.

Thereafter the mixture was pumped through a heat exchanger set at 190° F. and allowed to travel through a pipe coil for 25 minutes. The mixture was then pumped to a horizontal decanting centrifuge set at 3,600 RPM and fed at a rate of two gallons per minute. The soluble fraction of the rice bran was separated from the insoluble fraction in the centrifuge.

Thereafter the soluble fraction was dried on a drum dryer to 2.8% moisture. The insoluble fraction was also dried on a drum dryer to 4% moisture. This process yielded 550 lbs. of dried rice bran insolubles and 420 lbs. of dried rice bran soluble concentrate. The chemical composition of the two products are set forth in Tables IV and V respectfully.

Example 4

This example sets forth Tables IV–VII which tabulates components of stabilized rice bran derivatives.

TABLE IV

RiceX ™ FIBER COMPLEX

| MACRONUTRIENTS | |
|---|---|
| Protein | 20.5% |
| Fat | 13.4% |
| Total Dietary Fiber | 49.5% |
| (Soluble Fiber 0–1%) | |
| Carbohydrates | 3.0% |
| Ash | 10.0% |
| Moisture | 3.5% |
| MICRONUTRIENTS | |
| Water Soluble Vitamins (mg/100 Grams) | Average |
| Thiamine | 2.00 |
| Riboflavin | 0.19 |
| Niacin | 30.55 |
| Pantothenic Acid | 1.90 |
| Vitamin $B_6$ | 1.67 |
| Biotin | 0.011 |
| Minerals (mg/100 Grams) | Average |
| Sodium | 16.0 |
| Calcium | 92.5 |
| Magnesium | 1223.3 |
| Potassium | 1670.0 |
| Vitamin E and Other "Tocol's" (mg/100 Grams) | Average |
| α-Tocopherol | 0.74 |
| τ-Tocopoherol | 0.40 |
| δ-Tocopherol | 0.43 |
| Total Tocopherols | 1.19 |
| Tocopherols | |
| α-Tocopherol | 0.59 |
| β-Carotene | 1.55 |
| τ-Tocopoherol | 1.60 |
| δ-Tocopherol | 0.19 |
| Total Tocopherols | 2.54 |
| Total TOCOLS | 3.73 |
| Vitamin A and Other Carotenoids (μg/100 Grams) | Average |
| α-Carotene | TBD |
| β-Carotene | TBD |
| Lycopene | TBD |
| Pre-Lutein | TBD |
| Lutein | TBD |
| Zeaxantin | TBD |

TABLE IV-continued

RiceX™ FIBER COMPLEX

| | |
|---|---|
| Pre-Cryptoxanthin | TBD |
| Cryptoxanthin | TBD |
| β-Cryptoxanthin | TBD |
| Total CAROTENOIDS | TBD |
| τ-Oryzanol (mg/100 Grams) | Average |
| | 174.1 |
| Phytosterols (mg/100 Grams) | Average |
| Sitosterol | 146.46 |
| Brassicasterol | 13.20 |
| Campesterol | 90.40 |
| Stigmesterol | 67.15 |
| Total PHYTOSTEROLS | 317.2 |

TABLE V

RiceX RICELIN™

| MACRONUTRIENTS | |
|---|---|
| Protein | 7.5% |
| Fat | 26.5% |
| Total Dietary Fiber | 3.0% |
| Carbohydrates | 54.5% |
| Ash | 5.0% |
| Moisture | 3.0% |
| MICRONUTRIENTS | |
| Water Soluble Vitamins (mg/100 Grams) | Average |
| Thiamine | 3.64 |
| Riboflavin | 0.46 |
| Niacin | 76.6 |
| Pantothenic Acid | 5.82 |
| Vitamin $B_6$ | 5.81 |
| Biotin | 0.015 |
| Minerals (mg/100 Grams) | Average |
| Sodium | 15.75 |
| Calcium | 8.33 |
| Magnesium | 170.8 |
| Potassium | 1562.0 |
| Vitamin E and Other "Tocol's" (mg/100 Grams) | Average |
| α-Tocopherol | 6.80 |
| τ-Tocopoherol | 1.13 |
| δ-Tocopherol | 0.07 |
| Total Tocopherols | 8.00 |
| α-Tocotrienol | 4.90 |
| β-Tocotrienol | 0.36 |
| τ-Tocotrienol | 4.48 |
| δ-Tocotrienol | 0.30 |
| Total Tocotrienols | 10.0 |
| Total TOCOLS | 18.0 |
| Vitamin A and Other Carotenoids (μg/100 g) | Average |
| α-Carotene | TBD |
| β-Carotene | TBD |
| Lycopene | TBD |
| Pre-Lutein | TBD |
| Lutein | TBD |
| Zeaxantin | TBD |
| Pre-Cryptoxanthin | TBD |
| Cryptoxanthin | TBD |
| β-Cryptoxanthin | TBD |
| Total CAROTENOIDS | TBD |
| τ-Oryzanol (mg/100 Grams) | Average |
| | 248.1 |

TABLE V-continued

RiceX RICELIN™

| | |
|---|---|
| Phytosterols (mg/100 Grams) | Average |
| Sitosterol | 211.90 |
| Brassicasterol | 15.20 |
| Campesterol | 117.32 |
| Stigmesterol | 68.69 |
| Total PHYTOSTEROLS | 385.0 |

TABLE VI

RiceX™ STABILIZED RICE BRAN

| MACRONUTRIENTS | |
|---|---|
| Protein | 14.5% |
| Fat | 20.5% |
| Total Dietary Fiber (Soluble Fiber 2–6%) | 29.0% |
| Carbohydrates | 22.0% |
| Ash | 8.0% |
| Moisture | 6.0% |
| MICRONUTRIENTS | |
| Water Soluble Vitamins (mg/100 Grams) | Average |
| Thiamine | 2.65 |
| Riboflavin | 0.28 |
| Niacin | 46.87 |
| Pantothenic Acid | 3.98 |
| Vitamin $B_6$ | 3.17 |
| Biotin | 0.014 |
| Minerals (mg/100 Grams) | Average |
| Sodium | 8.0 |
| Calcium | 39.7 |
| Magnesium | 727.0 |
| Potassium | 1573.0 |
| Vitamin E and Other "Tocol's" (mg/100 Grams) | Average |
| α-Tocopherol | 10.60 |
| τ-Tocopoherol | 1.34 |
| δ-Tocopherol | 0.07 |
| Total Tocopherols | 11.97 |
| α-Tocotrienol | 7.56 |
| β-Tocotrienol | 0.41 |
| τ-Tocotrienol | 5.36 |
| δ-Tocotrienol | 0.31 |
| Total Tocotrienols | 13.60 |
| Total TOCOLS | 25.61 |
| Vitamin A and Other Carotenoids (μg/100 Grams) | Average |
| α-Carotene | 0.4 |
| β-Carotene | 37.0 |
| Lycopene | 2.3 |
| Pre-Lutein | ND |
| Lutein | 63.8 |
| Zeaxantin | 18.4 |
| Pre-Cryptoxanthin | 7.4 |
| Cryptoxanthin | ND |
| β-Cryptoxanthin | ND |
| Total CAROTENOIDS | 129.3 |
| τ-Oryzanol (mg/100 Grams) | Average |
| | 245.15 |
| Phytosterols (mg/100 Grams) | Average |
| Sitosterol | 151.47 |
| Brassicasterol | 14.61 |
| Campesterol | 91.57 |
| Stigmesterol | 58.59 |
| Total PHYTOSTEROLS | 302 |

TABLE VII

Antioxidants in RiceX ™ STABILIZED RICE BRAN

A. τ-Oryzanol: (ppm)

(2206–3000)
Cycloartenyl Ferulate
24-Methylene Cycloartanyl
Ferulate
Campesteryl Ferulate
β-Sitosteryl Ferulate
Stigmasteryl Ferulate
B. Tocopherols & Tocotrienols:

(220–320 ppm)
α-Tocopherol
β-Tocopherol
τ-Tocopherol
δ-Tocopherol
α-Tocotrienol
β-Tocotrienol
τ-Tocotrienol
Tocotrienols (Artifacts)
C. Phytosterols: (2230–4400 ppm) 4-Demethylsterols, 4-Methyl Sterol & Brassino Steroids β-Sitosterol
Campesterol
Stigmasterol
Δ5 Avinsterol
Δ7 Stigmastenol
Isofucosterol
β-Amyrin
Gramisterol
Citrostadienol
Obtusifoliol
Branosterol
28-Homotyphasterol
28-Homosteasternoic Acid
6-Deoxycastasterone
D. Amino Acids: (ppm)

Tryptophan (2100)
Histidine (3800)
Methionine (2500)
Cystine (336–448)
Cysteine (3200)
Arginine (10800)
E. Polyphenols:

α-Lipoic Acid
Ferulic Acid
Methyl Ferulate
p-Coumaric Acid
p-Sinapic Acid
F. Flavones and Proanthocyanidins Iso Vitexin
Flavone Glycosides
Olegomeric
Proanthocyanidins
G. Other Antioxidants: (ppm)

Inositol/Myo Inositol
(1200–1880)
Phytic Acid/Phytates
(1500–1710)
Biotin (0.1–0.22)
Choline (930–1150)
H. Carotenoids: (0.9–1.6 ppm)

α-carotene
β-carotene
Lycopene

TABLE VII-continued

Antioxidants in RiceX ™ STABILIZED RICE BRAN

Lutein
Zeasanthine
I. Phospholipids:

Phosphatidyl Choline
Phosphatidyl Ethanolamine
Lysolecithin
J. Enzymes:

Glutathione Peroxidase
Methionine Reductase
Super Oxide Dismutase
Polyphenol Oxidase
Aspartate Amino Transferase
Isoenzyme
AAT-1
AAT-2
Coenzyme Q10
K. Polysaccharides:

Cycloartenol Ferulic Acid
Glycoside
Diferulic Acid Complex
Diferulic Acid + 3
Glucose + 2
Calcium ions complex
L. Metal Chelators: (ppm)

Magnesium (6250–8440)
Calcium (303–500)
Phosphorous (14700–17000)
M. B-Complex Vitamins: (ppm)

Thiamine (22–31)
Riboflavin (2.2–3.5)
Niacin (370–660)
Pantothenic Acid (36–50)
Pyridoxine (29–42)

All publications, patents and patent applications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A method for controlling serum glucose in a mammal, said method comprising:

ingesting a therapeutically effective amount of a stabilized rice bran solubilized fraction, wherein said stabilized rice bran solubilized fraction is free of a stabilized rice bran insolubilized fraction, thereby reducing serum glucose in said mammal.

2. A method for controlling serum glucose in a mammal, said method comprising:

ingesting a therapeutically effective amount of a stabilized rice bran insolubilized fraction, wherein said stabilized rice bran insolubilized fraction is free of a stabilized rice bran solubilized fraction, thereby reducing serum glucose in said mammal.

3. A method in accordance with claim 1 or 2, wherein said mamnmnal is a human.

4. A method in accordance with claim 1 or 2, wherein said mammal is suffering from diabetes mellitus.

5. A method in accordance with claim 4, wherein said diabetes mellitus is Type I.

6. A method in accordance with claim 4, wherein said diabetes mellitus is Type II.

7. A method in accordance with claim 1, wherein said stabilized rice bran solubilized fraction comprises about 0% to about 20% total dietary fiber w/w.

8. A method in accordance with claim 2, wherein said stabilized rice bran insolubilized fraction comprises about 40% to about 60% total dietary fiber content w/w.

9. A method in accordance with claim 1 or 2, wherein said fraction is ingested in an amount of about 10 grams to about 100 grams per day total.

10. A method in accordance with claim 9, wherein said amount is ingested in at least 2 doses.

11. A method in accordance with claim 9, wherein said amount is about 10 grams to about 40 grams per day total.

* * * * *